US006592881B1

(12) United States Patent
Fukuda et al.

(10) Patent No.: US 6,592,881 B1
(45) Date of Patent: Jul. 15, 2003

(54) SEBUM REMOVING METHOD

(75) Inventors: Masataka Fukuda, Tokyo (JP);
Yasunobu Matsumoto, Tokyo (JP);
Tomoko Kondo, Tokyo (JP)

(73) Assignee: Kao Corporation, Tokyo (JP)

( * ) Notice: Subject to any disclaimer, the term of this patent is extended or adjusted under 35 U.S.C. 154(b) by 270 days.

(21) Appl. No.: 09/305,746

(22) Filed: May 6, 1999

(30) Foreign Application Priority Data

May 14, 1998 (JP) ............................. 10-131699

(51) Int. Cl.[7] .............................. A61K 6/00; A61K 7/00
(52) U.S. Cl. ................... 424/401; 424/70.8; 424/400
(58) Field of Search ................. 424/400, 401, 424/520, 450, 43, 47, 70.8; 514/844, 845, 846, 847, 848; 132/286; 206/542

(56) References Cited

U.S. PATENT DOCUMENTS

| 4,367,227 A | * | 1/1983 | Bingham ................ 424/243 |
| 5,462,691 A | * | 10/1995 | Shimada et al. ....... 252/174.15 |
| 5,472,699 A | * | 12/1995 | Duffy et al. ................ 424/401 |

* cited by examiner

*Primary Examiner*—Dameron L. Jones
(74) *Attorney, Agent, or Firm*—Oblon, Spivak, McClelland, Maier & Neustadt, P.C.

(57) ABSTRACT

Described is a sebum removing method which comprises applying a liquid composition to the skin and holding a water absorptive or oil absorptive material against the surface of the applied skin to remove sebum together with the liquid composition. According to this method, sebum can be removed from the skin effectively and selectively without removing makeup from the made-up face.

13 Claims, No Drawings

SEBUM REMOVING METHOD

BACKGROUND OF THE INVENTION

1. Field of the Invention

The present invention relates to a method for removing sebum from the skin, more specifically, a method for not only removing sebum from the skin before makeup but also selectively removing sebum even from the made-up skin without removing makeup, and also to a method for adjusting makeup.

2. Description of the Related Art

Many women complain that excess secretion of sebum makes their face, particularly, forehead, nose or chin oily or sticky and ruins their makeup. As a sebum removing method, frequent face cleansing or use of sebum removing paper by holding it against the face is conventionally known. Although face cleansing has high sebum removing effects, it removes not only the sebum but also the foundation or lipstick without selectivity. Therefore the makeup of the face must be started from the beginning again after cleansing, leading to a problem of inconvenience. In addition, use of a cleansing agent having high detergency or frequent face washing tends to make the skin rough, taut or excessively dry.

Sebum removing paper, on the other hand, can remove sebum selectively and easily without removing the makeup from the made-up face so that it has been popular as a usual makeup adjusting method. But, users have often expressed dissatisfaction with it, because owing to relatively low sebum removing effects, the face becomes oily soon after use or plural sheets of paper must be used each time.

An object of the present invention is therefore to provide a method for removing sebum selectively and effectively from the skin without removing the makeup from the made-up face.

SUMMARY OF THE INVENTION

In one aspect of the present invention, there is thus provided a selective sebum removing method which comprises applying a liquid composition to the skin, holding a water absorptive or oil absorptive material against the surface of the skin, thereby removing the sebum together with the liquid composition.

In another aspect of the present invention, there is also provided a makeup adjusting method which comprises applying a liquid composition to the skin, holding a water or oil absorptive material against the skin and then adjusting makeup.

According to the present invention, sebum can be removed simply and easily without removing the makeup from the made-up face. In addition, the method of the present invention brings about high sebum removing effects, which makes it possible to remove stickiness or sebum-induced shining and impart the skin with dry tough feeling. When the makeup is adjusted, therefore, good makeup spread can be attained and makeup retention after adjustment is also good. The method of the present invention is also suited for the removal of sebum from the not made-up skin.

EMBODIMENTS OF THE INVENTION

There is no particular limitation imposed on the liquid composition to be used in the present invention insofar as it is in a liquid form at room temperature. Any one of purified water and aqueous and oily liquid compositions containing a component ordinarily employed for a cosmetic composition can be used. Among them, aqueous liquid compositions are preferred because they impart the skin with dry and refreshed touch feelings after sebum removal.

It is preferred to incorporate a hydrophilic surfactant and/or ethanol in the aqueous liquid composition. Here, as the hydrophilic surfactant, any one of nonionic surfactants, anionic surfactants, amphoteric surfactants and cationic surfactants can be employed.

Examples of the nonionic surfactant include polyoxyethylene addition type surfactants such as polyoxyethylene castor oil or polyoxyethylene hydrogenated castor oil derivatives, polyoxyethylene sorbitan fatty acid esters, fatty acid esters of polyoxyethylene glycol, polyoxyethylene sorbitol fatty acid esters, polyoxyethylene alkyl ethers, polyoxyethylene alkyl phenyl ethers and polyoxyethylene polyoxypropylene block polymers; polyglycerin alkyl ethers, polyglycerin fatty acid esters, sucrose fatty acid esters and alkyl glucosides.

Examples of the anionic surfactants include N-acylamino acid salts such as sodium lauroyl sarcosinate and sodium lauroyl methyl alanine; polyoxyethylene alkylether phosphates, polyoxyethylene alkylsulfates, alkyl sulfates, alkylphosphates and fatty acid salts.

Examples of the amphoteric surfactant include alkylbetaines and alkylamidobetaines.

Examples of the cationic surfactant include di(long-chain alkyl) quaternary ammonium salts, mono(long-chain alkyl) quaternary ammonium salts, bis(hydroxyalkyl) quaternary ammonium salts, and amide/ester-group-containing quaternary ammonium salts.

Among the above-exemplified hydrophilic surfactants, preferred is that having a contact angle of 60° or less when measured 20 seconds after the dropwise addition of 1.2 µL of it in the form of a 0.5 wt. % aqueous solution onto a polyurethane-made artificial skin ("Bioskin No. F-910", trade name; product of Viewlux). In the present invention, the contact angle is a value as measured by a contact angle measuring meter (Kyowa Kaimen Kagakusha).

The hydrophilic surfactants can be used either singly or in combination. It is preferred to add the hydrophilic surfactant (s) to the liquid composition in a total amount of 0.001 to 5 wt. %, particularly 0.01 to 3 wt. %, because in such an amount, particularly good touch feeling of the skin can be attained after sebum removal.

Ethanol is preferably added in an amount of 0.01 to 20 wt. %, particularly 0.05 to 10 wt. % to the liquid composition from the viewpoints of enough sebum removing effects and low skin irritation.

When the oily liquid composition is used as the liquid composition, on the other hand, an oily component can be incorporated therein. Examples of the oily component include hydrocarbon oils such as solid or liquid paraffin, vaseline and squalane; natural oils and fats such as eucalyptus oil, beef tallow, olive oil and jojoba oil; ester oils such as isopropyl myristate and neopentyl glycol dicaprate; higher fatty acids such as stearic acid and linoleic acid; higher alcohols such as cetanol and stearyl alcohol; phospholipids; naturally extracted sphingosine derivatives and synthesized products thereof; cholesterol derivatives such as cholesterol and cholesteryl isostearate; silicones such as methyl polysiloxane and methyl phenyl polysiloxane; cyclic silicones, modified silicones such as oxazoline modified silicone; and amide derivatives as described in Japanese Patent Applications Laid-Open Nos. Hei 8-319263 and Sho 62-228048.

In addition to the above-described component, components ordinarily employed for a cosmetic composition can be incorporated optionally in the above-described aqueous or oily liquid composition within an extent not damaging the advantages of the present invention. Examples include oils, humectants, water-soluble polymers, acids, bases, salts, perfumes, colorants, antioxidants, ultraviolet absorbers, whitening agents, blood circulation promoters, vitamins, metal chelating agents, sebum controlling agents, powders, astringents, skin softeners, cool-touch imparting agents, anti-inflammatory agents, proteins, amino acids and vegetable extracts. The liquid composition of the present invention can be prepared in the conventional manner.

A liquid composition having a contact angle of 80° or less, particularly 60° or less as measured in a similar manner to the above is preferred, because it fits well when applied to the skin.

In the present invention, first, such a liquid composition is applied to the skin by a method other than spraying. There is no particular limitation imposed on the applying method of the liquid composition insofar as it can be spread over the surface of the skin. Examples of the method which can be adopted include application by hands, application by a tool such as roller or brush and application by cotton or a tissue paper impregnated with a sufficient amount of the liquid composition. An average application amount of the liquid composition, particularly, aqueous liquid composition per unit area is preferably 0.01 to 50 mg/cm$^2$, particularly 0.05 to 30 mg/cm$^2$ from the viewpoints of sebum removing effects and cosmetic retention.

In the next step, a water absorptive or oil absorptive material is held against the part to which the liquid composition has been applied. Examples of the water absorptive or oil absorptive material include a polymer gel, porous material and fibrous material. They can be used either singly or in combination.

Specific examples of the polymer gel include acrylic acid series water absorptive polymers. Those of the porous material include polymer materials such as polyamide and mineral materials such as silica. They can be used in the form of a sponge, sheet or puff. Specific examples of the fibrous material include pulp, hemp, cotton, rayon, acetate, acryl, polyester, polyethylene, polypropylene, polyurethane and polyamide. They can be used after compression molding or forming, into a mass. Specific examples of the form include paper such as facial tissue, woven cloth, nonwoven cloth and facial cotton. By holding such a material against the skin, sebum can be removed selectively together with the applied liquid composition. It is preferred to use the water absorptive material and oil absorptive material when the aqueous liquid composition and oily liquid composition are used as the liquid composition, respectively.

Wiping of the surface of the skin with the above-described material is however not preferred, because it happens to remove the makeup partially.

Good makeup spread, beautiful finish and good cosmetic retention after makeup can be attained by the cosmetic adjustment in the ordinarily employed manner after the liquid composition is applied to the made-up skin and then a water absorptive or oil absorptive material is held against the applied surface.

EXAMPLES

The present invention will next be described more specifically by examples.

Example 1

Purified water (about 125 mg) was applied to a face with hands to spread it substantially uniformly all over the face and right after application, a tissue paper was held against the face.

Examples 2 to 7

In each of Examples 2 to 7, the liquid composition as shown in Table 1 was prepared in the conventional manner. The resulting liquid composition (about 125 mg) was applied to a face with hands to spread it substantially uniformly all over the face. Right after application, a tissue paper was held against the face.

The application amount of the liquid composition per unit area was 0.48 mg/cm$^2$ as a result of determination from the below-described equation.

Amount (mg/cm$^2$) per unit area=amount (mg) applied to the whole face / surface area of the face (cm$^2$)

Here, the surface area of the face was found from the following equation:

$$\text{Area of the face } S \text{ (cm}^2\text{)} = \pi \cdot \frac{a}{2} \cdot \frac{b}{2}$$

a=average of "bizygomatic breadth A7", as described on page 78 of the below-described literature, of 50 percentiles of young and matured males and females b=average of "whole height of head A36", as described on page 92 of the below-described literature, of 50 percentiles of young and matured males and females $\pi$=the circular constant a=142.5 mm b=230.75 mm The area of the face S=258 cm$^2$ <Literature> "Body Size Data for Designing" ed. by: National Institute of Bioscience and Human Technology/Agency of Industrial Science and Technology/Ministry of International Trade and Industry published by: Research Institute of Human Engineering for Quality Life Sold from: Nippon Publishing Service Co., Ltd.

TABLE 1

| Component (wt. %) | Ex. 2 Composition A | Ex. 3 Composition B | Ex. 4 Composition C | Ex. 5 Composition D | Ex. 6 Composition E | Ex. 7 Composition F |
|---|---|---|---|---|---|---|
| Diester of polyoxyethylene glyceryl glutamic acid and isostearic acid (25EO) [*1] | 0.8 | 0.8 | — | — | — | — |
| Polyoxyethylene hydrogenated castor oil (60EO) [*2] | — | — | 0.8 | — | — | — |
| Palmitic acid [*3] | — | — | — | — | 0.45 | — |
| Stearic acid [*4] | — | — | — | — | 0.55 | — |
| Potassium hydroxide | — | — | — | — | 0.27 | — |
| 95% ethanol | 5 | — | — | 5 | — | — |
| Rosemary extract | 0.5 | 0.5 | 0.5 | 0.5 | 0.5 | — |
| 2-(2-hydroxyethoxy) ethylguanidine [*5] | 0.05 | 0.05 | 0.05 | 0.05 | 0.05 | — |

TABLE 1-continued

| Component (wt. %) | Ex. 2 Composition A | Ex. 3 Composition B | Ex. 4 Composition C | Ex. 5 Composition D | Ex. 6 Composition E | Ex. 7 Composition F |
|---|---|---|---|---|---|---|
| Menthol | 0.05 | 0.05 | 0.05 | 0.05 | 0.05 | — |
| Glycerin | 1 | 1 | 1 | 1 | 1 | — |
| Citric acid | 0.05 | 0.05 | 0.05 | 0.05 | 0.05 | — |
| Sodium citrate | 0.05 | 0.05 | 0.05 | 0.05 | 0.05 | — |
| Methyl paraoxybenzoate | 0.1 | 0.1 | 0.1 | 0.1 | 0.1 | — |
| Perfume | Trace | Trace | Trace | Trace | Trace | Trace |
| Squalane | — | — | — | — | — | 10.0 |
| Liquid isoparaffin | — | — | — | — | — | 29.0 |
| Methyl polysiloxane | — | — | — | — | — | 30.0 |
| Methyl cyclopolysiloxane | — | — | — | — | — | 30.0 |
| 99.8% ethanol | — | — | — | — | — | 1.0 |
| Purified water | Balance | Balance | Balance | Balance | Balance | — |
| Contact angle of composition | 50° | 53° | 56° | 78° | 48° | <30° |

*1 contact angle: 55°
*2 contact angle: 62°
*3 contact angle: 50° as potassium palmitate
*4 contact angle: 52° as potassium stearate.
*5 prepared in accordance with Example 1 of Japanese Patent Application Laid-Open No. Hei 7-170628

Example 8

The liquid composition A (about 125 mg) similar to that used in Example 2 was applied to a face with hands so as to spread it substantially uniformly over the whole face. Right after the application, a facial cotton was held against the face.

Example 9

The liquid composition A (about 125 mg) similar to that used in Example 2 was applied, by a cotton impregnated therewith, to a face so as to spread it substantially uniformly all over the face. Right after the application, a tissue paper was held against the face.

Example 10

An aqueous liquid composition (G) having the below-described composition was prepared in a conventional manner. An about 125 mg portion of it was applied to a face with hands so as to spread it substantially uniformly all over the face. Right after the application, a tissue paper was held against the face.

| (Components) | (wt. %) |
|---|---|
| Polyoxyethylene isocetyl ether (20EO) (contact angle: 35°) | 1.2 |
| Peppermint extract | 1.0 |
| 1-Menthyl lactate | 0.05 |
| Urea | 0.05 |
| ε-Aminocaproic acid | 0.01 |
| 1,3-Butanediol | 1.0 |
| Polyethylene glycol 1500 | 2.0 |
| Succinic acid | 0.1 |
| Disodium phosphate | 0.2 |
| Benzoic acid | 0.3 |
| Acid polysaccharide (acid polysaccharide induced from the callus of tuberous and prepared in accordance with Example 1 of Japanese Patent Application Laid-Open No. Sho 64-10997) | 1.0 |
| 95% Ethanol | 5.0 |
| Perfume | Trace |
| Purified water | Balance |

Example 11

An aqueous liquid composition (H) having the below-described composition was prepared in a conventional manner. An about 125 mg portion of the resulting composition was applied to a face with hands so as to spread it substantially uniformly all over the face. Right after the application, a tissue paper was held against the face.

| (Components) | (wt. %) |
|---|---|
| Polyethylene glycol monolaurate (contact angle: 40°) | 1.5 |
| 1-Menthyl glyceryl ether | 0.05 |
| Tris(ethoxyethoxyethyl)phosphate | 2.0 |
| Polyethylene glycol 1500 | 2.0 |
| Succinic acid | 0.1 |
| Disodium phosphate | 0.2 |
| Benzoic acid | 0.3 |
| Zinc p-phenolsulfonate | 0.05 |
| Perfume | Trace |
| Purified water | Balance |

Example 12

An aqueous liquid composition (I) having the below-described composition was prepared in a conventional manner. An about 125 mg portion of the resulting composition was applied to a face with hands so as to spread it substantially uniformly all over the face. Right after the application, a tissue paper was held against the face.

| (Components) | (wt. %) |
|---|---|
| Polyoxyethylene isocetyl ether (20EO) (contact angle: 35°) | 1.0 |
| Neopentyl glycol dicaprate | 0.5 |
| Citric acid | 0.2 |
| Sodium citrate | 0.3 |
| 1,3-Propanediol | 1.2 |
| Glycerin | 1.0 |
| Methyl paraoxybenzoate | 0.2 |
| Purified water | Balance |

Comparative Example 1

After application of a foundation, sebum removal was not carried out at all.

Comparative Example 2

Sebum was removed in an ordinary manner by using sebum removing paper.

Comparative Example 3

A liquid composition A (about 125 mg) similar to that used in Example 2 was applied to a face with hands so as to spread it substantially uniformly all over the face. Then, nothing was held against the face.

Comparative Example 4

A liquid composition A (about 125 mg) similar to that used in Example 2 was applied to a face with hands so as to spread it substantially uniformly all over the face. After the application, the face was wiped with a tissue paper.

Test 1

With regards to the sebum removing operations carried out in Examples 1 to 12 and Comparative Examples 1 to 4, the sebum removing effect (remaining amount of sebum), selectivity to sebum, dry touch feeling rightly after the operation, makeup spread and makeup retention were evaluated. The results are shown in Tables 2 and 3.

(Evaluation Methods)

(1) Sebum Removing Effect (Remaining Amount of Sebum)

After face cleansing, foundation was applied to the face. Four hours later, one side of the forehead [designated as an untreated portion (Comparative Example 1)] was not subjected to any sebum removing operation while the other side was subjected to any one of the operations in Examples 1 to 12 and Comparative Examples 2 and 4. Right after the treatment, sebum in a predetermined area of each portion of the forehead was extracted with acetone/ether (50:50). The resulting solution was filtered, followed by concentration to dryness. The solid was then re-dissolved in hexane at a fixed dilution ratio. The resulting solution was subjected to gas chromatography, whereby an amount of squalene per 1 $cm^2$ of each portion of the forehead was determined.

The amount of squalene obtained by each operation (each of Examples 1 to 12 and Comparative Examples 2 to 4) was calculated with that of the untreated portion (Comparative Example 1) as 100 and it was designated as the remaining amount of sebum (%). The results are shown as an average value of 10 samples.

(2) Selectivity to Sebum

Twenty women who had usually experienced makeup fading due to sebum were asked if they felt uneasy about the coming-off of the foundation after each of the sebum removing operations. Each operation was judged based on the following standards.

A: Two out of 20 women answered yes.

B: At least 3 but not greater than 5 out of 20 women answered yes.

C: At least 6 out of 20 women answered yes.

(3) Dry Touch Feeling Rightly after the Operation, Makeup Spread Upon Adjustment of Makeup and Makeup Retention after Adjustment.

Twenty women who had usually experienced makeup fading due to sebum and therefore used, sebum removing paper were asked to evaluate, as touch feeling of the skin after removal of sebum by each of the sebum removing operations, dry touch feeling rightly after the operation, makeup spread upon adjustment of makeup and makeup retention after adjustment in comparison with the daily operation. Evaluations were judged based on the following standards:

A: Out of 20 women, 16 answered good.

B: Out of 20 women, at least 12 but less than 16 answered good.

C: Out of 20 women, at least 8 not less than 12 answered good.

D: Out of 20 women, not less than 8 answered good.

As a result, as shown in Tables 2 and 3, it has been found that sebum was removed selectively and no sebum fading occurred when the method of the present invention was employed. In the case where the amount of the liquid composition applied per unit area of the skin was less than 0.01 $mg/cm^2$ (for example, 0.005 $mg/cm^2$), sebum removing effects were not sufficient and amounts exceeding 50 $mg/cm^2$ (for example, 70 $mg/cm^2$) tend to cause makeup fading.

TABLE 2

| | Examples | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Liquid composition to be employed | Purified water | A | B | C | D | E | F | A | A | G | H | I |
| Material to be held against the skin | Tissue paper | Tissue paper | Tissue paper | Tissue paper | Tissue paper | Tissue paper | Tissue paper | Handkerchief (cotton) | Facial cotton | Tissue paper | Tissue paper | Tissue paper |
| Remaining amount of sebum (%) | 50 | 32 | 33 | 40 | 35 | 35 | 53 | 35 | 37 | 30 | 31 | 35 |
| Selectivity to sebum | A | A | A | A | A | A | A | A | A | A | A | A |
| Dry touch feeling rightly after application | B | A | A | B | A | A | B | A | A | A | A | A |
| Makeup spread | B | A | A | A | A | A | B | A | A | A | A | A |
| Makeup retention | B | A | A | B | A | A | B | A | A | A | A | A |

TABLE 3

| | Comparative Examples | | | |
|---|---|---|---|---|
| | 1 | 2 | 3 | 4 |
| Liquid composition To be employed | — | — | A | A |
| Material to be held against the skin | — | Sebum removing paper | — | Rubbing with Facial tissue |

TABLE 3-continued

| | Comparative Examples | | | |
|---|---|---|---|---|
| | 1 | 2 | 3 | 4 |
| Remaining amount of sebum (%) | 100 | 63 | 102 | 39 |
| Selectivity to sebum | A | A | A | B |
| Dry touch feeling rightly after application | D | C | D | C |
| Makeup spread | D | C | C | C |
| Makeup retention | D | C | C | C |

Japanese Patent Application No. 10-131699 filed on May 14, 1998, is incorporated herein by reference.

What is claimed is:

1. A method for removing sebum selectively from the skin of a made-up face without removing makeup, which comprises applying a liquid composition to the skin by a technique other than spraying, followed by holding a water absorptive or oil absorptive material against the skin without wiping such that sebum and said liquid composition are selectively removed from the made up face.

2. A method according to claim 1, wherein the liquid composition is an aqueous liquid composition and the water absorptive material is held against the skin.

3. A method according to claim 2, wherein the aqueous liquid composition contains a hydrophilic surfactant and/or ethanol.

4. A method according to claim 3, wherein the average application amount of the aqueous liquid composition per unit area is 0.01 to 50 mg/cm$^2$.

5. A method according to claim 1 wherein the liquid composition has a contact angle of 80° or less when measured 20 seconds after the dropwise addition of 1.2 µL of the composition onto a polyurethane-made artificial skin.

6. The method according to claim 3, wherein said aqueous liquid composition contains a hydrophilic surfactant selected from the group consisting of nonionic surfactants, anionic surfactants, amphoteric surfactants, and cationic surfactants.

7. A method according to claim 6, wherein said hydrophilic surfactant is present in said liquid composition in a total amount of 0.001 to 5 wt. %.

8. The method of claim 3, wherein said aqueous liquid composition comprises ethanol in an amount of 0.01 to 20 wt. %.

9. The method according to claim 1, wherein the liquid composition is an oily composition comprising an oily component, and wherein an oil absorptive material is held against the skin.

10. The method as claimed in claim 1, wherein said water absorptive or oil absorptive material is selected from the group consisting of polymer gel, a porous material and a fibrous material.

11. The method as claimed in claim 1, wherein said water absorptive or oil absorptive material is an acrylic acid water absorptive polymer.

12. The method of claim 1, wherein said water absorptive or oil absorptive material is tissue paper.

13. The method as claimed in claim 1, wherein said liquid composition comprises a material selected from the group consisting of a diester of polyoxyethylene glyceryl glutamic acid and isostearic acid, polyoxyethylene hydrogenated castor oil, palmitic acid, stearic acid, squalane, liquid isoparaffin, methyl polysiloxane, methyl cyclopolysiloxane, polyoxyethylene isocetyl ether, and polyethylene glycol monolaurate.

* * * * *